US009643900B2

(12) United States Patent
Arriola et al.

(10) Patent No.: US 9,643,900 B2
(45) Date of Patent: May 9, 2017

(54) HYPERBRANCHED ETHYLENE-BASED OILS AND GREASES

(71) Applicant: Dow Global Technologies LLC, Midland, MI (US)

(72) Inventors: Daniel J. Arriola, Midland, MI (US); Brad C. Bailey, Midland, MI (US); Jerzy Klosin, Midland, MI (US); Zenon Lysenko, Midland, MI (US); Gordon R. Roof, Midland, MI (US); Austin J. Smith, Saginaw, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/893,732

(22) PCT Filed: Jun. 24, 2014

(86) PCT No.: PCT/US2014/043754
§ 371 (c)(1),
(2) Date: Nov. 24, 2015

(87) PCT Pub. No.: WO2014/209927
PCT Pub. Date: Dec. 31, 2014

(65) Prior Publication Data
US 2016/0122259 A1  May 5, 2016

Related U.S. Application Data

(60) Provisional application No. 61/840,622, filed on Jun. 28, 2013.

(51) Int. Cl.
| | |
|---|---|
| *C07C 2/34* | (2006.01) |
| *C08F 10/00* | (2006.01) |
| *C10M 105/00* | (2006.01) |
| *B01J 31/00* | (2006.01) |
| *C10M 107/02* | (2006.01) |
| *C10M 107/04* | (2006.01) |
| *C10M 107/10* | (2006.01) |

(52) U.S. Cl.
CPC ............. *C07C 2/34* (2013.01); *B01J 31/00* (2013.01); *C08F 10/00* (2013.01); *C10M 105/00* (2013.01); *C10M 107/02* (2013.01); *C10M 107/04* (2013.01); *C10M 107/10* (2013.01); *C07C 2531/22* (2013.01); *C10M 2203/02* (2013.01); *C10M 2205/0225* (2013.01); *C10M 2205/0285* (2013.01); *C10N 2220/028* (2013.01); *C10N 2250/10* (2013.01); *C10N 2270/00* (2013.01)

(58) Field of Classification Search
CPC C10M 105/00; C10M 107/02; C10M 107/04; C10M 107/10; C07C 2/34; B01J 31/00; C08F 10/00
USPC ........................ 556/21, 51, 54, 56
See application file for complete search history.

(56) References Cited

U.S. PATENT DOCUMENTS

| | | |
|---|---|---|
| 4,855,526 A | 8/1989 | Hen |
| 4,892,851 A | 1/1990 | Ewen et al. |
| 5,017,714 A | 5/1991 | Welborn, Jr. |
| 5,132,281 A | 7/1992 | Chevallier et al. |
| 5,155,080 A | 10/1992 | Elder et al. |
| 5,278,264 A | 1/1994 | Spaleck et al. |
| 5,296,434 A | 3/1994 | Karl et al. |
| 5,318,935 A | 6/1994 | Canich et al. |
| 5,578,837 A | 11/1996 | Jackson et al. |
| 5,710,222 A | 1/1998 | Ewen et al. |
| 5,969,070 A | 10/1999 | Waymouth et al. |
| 6,117,962 A | 9/2000 | Weng et al. |
| 6,303,717 B1 | 10/2001 | Sen et al. |
| 6,376,409 B1 | 4/2002 | Burkhardt et al. |
| 6,376,412 B1 | 4/2002 | Burkhardt et al. |
| 6,380,120 B1 | 4/2002 | Burkhardt et al. |
| 6,635,715 B1 | 10/2003 | Datta et al. |
| 6,835,698 B2 | 12/2004 | Egawa et al. |
| 7,037,988 B2 | 5/2006 | De Boer et al. |

(Continued)

FOREIGN PATENT DOCUMENTS

| | | |
|---|---|---|
| WO | 93/19103 A1 | 9/1993 |
| WO | WO 2013/101376 A1 * | 7/2013 |

OTHER PUBLICATIONS

PCT/US2014/043754, International Preliminary Report on Patentability with a date of completion of Jun. 3, 2015.*
Spaleck, W., et al., "The Influence of Aromatic Substituents on the Polymerization Behavior of Bridged Zirconocene Catalysts", Organometallics, 1994, vol. 13, pp. 954-963.
Brintzinger, H., et al., "Ansa-Zirconocene Polymerization Catalysts with Annelated Ring Ligands—Effects on Catalytic Activity and Polymer Chain Lengths", Organometallics, 1994, vol. 13, pp. 964-970.
Braunschweig, H., et al., "Constrained geometry complexes—Synthesis and applications", Coordination Chemistry Reviews, 2006, 250, 2691-2720.
Shahid Murtuza, et al., "Tantalum- and Titanium-Based Catalytic Systems for the Synthesis of Hyperbranced Polyethene", Journal of The American Chemical Society, vol. 122, No. 9, Mar. 1, 2000, pp. 1867-1872.

(Continued)

*Primary Examiner* — Porfirio Nazario Gonzalez
(74) *Attorney, Agent, or Firm* — Husch Blackwell LLP

(57) ABSTRACT

A process to prepare a relatively inexpensive utility fluid comprises contacting together ethylene and a coordination-insertion catalyst and, optionally, an alpha-olefin, in a continuously-fed backmixed reactor zone under conditions such that a mixture of a hyperbranched oligomer and a branched oligomer is formed. The hyperbranched oligomer has an average of at least 1.5 methine carbons per oligomer molecule, and at least 40 methine carbons per one-thousand total carbons, and at least 40 percent of the methine carbons is derived from the ethylene, and the average number of carbons per molecule is from 25 to 100, and at least 25 percent of the hyperbranched oligomer molecules has a vinyl group and can be separated from the branched oligomer, which has an average number of carbons per molecule of up to 20. The coordination-insertion catalyst is characterized as having an ethylene/octene reactivity ratio up to 20 and a kinetic chain length up to 20 monomer units.

10 Claims, No Drawings

(56) References Cited

U.S. PATENT DOCUMENTS

| | | |
|---|---|---|
| 7,238,764 B2 | 7/2007 | De Boer et al. |
| 7,342,078 B2 | 3/2008 | Schottek et al. |
| 8,609,794 B2 | 12/2013 | Klosin et al. |
| 9,029,487 B2 | 5/2015 | Klosin et al. |
| 2014/0330056 A1 | 11/2014 | Klosin et al. |

OTHER PUBLICATIONS

PCT/US14/043754, International Search Report and Written Opinion with a mailing date of Oct. 7, 2014.
PCT/US14/043754, International Preliminary Report on Patentability with a mailing date of Jun. 3, 2015.
PCT/US14/043754, Response Written Opinion dated Jan. 7, 2015.

* cited by examiner

HYPERBRANCHED ETHYLENE-BASED OILS AND GREASES

CROSS-REFERENCE TO A RELATED APPLICATION

This application claims priority to U.S. Provisional Application Ser. No. 61/840,622, filed Jun. 28, 2013, which is incorporated herein by reference in its entirety.

The invention relates to utility fluids, and particularly to compositions and processes to make utility fluids by an olefin insertion oligomerization using ethylene.

The polymerization of ethylene, propylene and alpha-olefins by transition metal coordination-insertion catalysts leads principally to the formation of linear backbone polymers. However, linear backbone polymers do not always exhibit properties such as desirable rheology under given conditions. Rheological behavior is often important in identifying oils or greases that are suitable for use as, for example, lubricants, dielectric fluids, and the like. In view of this, researchers in the art have sought branched materials in an effort to better control rheological behavior.

An example of this is found in U.S. Pat. No. 6,303,717, wherein branch points are made in situ in a "chain walking" polymerization, so-called because it is believed that the catalyst center "walks" along the aliphatic chain to randomly create branch points or modify length. By such a mechanism nearly any carbon within a linear alpha-olefin may become a methine (IUPAC: methylylidene) branch point. In this patent ethylene- and olefin-based oils, including a highly branched ethylene monopolymer, are prepared using a class of nickel(II) and palladium(II) complexes of alpha-diimine ligands as catalysts. While these chain-walking catalysts may induce polymerization at relatively low temperatures, they unfortunately tend to produce low yields while leaving significant levels of metals in the final product.

Another example is found in U.S. Pat. No. 4,855,526, which describes materials including at least 20 mole percent (mol %) ethylene with alpha-olefin comonomers. These are made using an aluminum-titanium Ziegler-Natta coordination-insertion catalyst. In this patent the branches are produced by incorporation of the alpha-olefin and the backbone of the polymer is linear.

Additional examples of coordination-insertion polymerization include U.S. Pat. Nos. 7,238,764 and 7,037,988, which both disclose use of an olefin comonomer other than ethylene. U.S. Pat. No. 7,238,764 demonstrates use of a catalyst that has very low reactivity with respect to alpha-olefins when compared to its ethylene reactivity.

U.S. Pat. No. 6,835,698 describes production of ethylene-olefin based copolymers having a claimed range for ethylene-olefin diad level with ethylene levels in the product ranging from 23 mol % to 49 mol %. These materials are produced by a selection of catalyst packages that create an ethylene-olefin backbone fitting the specified diads level.

There remains a need in the art for convenient, efficient and controllable processes to tailor the rheological behavior of the product to a specific end use application.

In one aspect the invention provides a process to prepare a utility fluid composition comprising (1) contacting together ethylene and at least one coordination-insertion catalyst and, optionally, an alpha-olefin, wherein the coordination-insertion catalyst is a metal-ligand complex wherein the metal is selected from zirconium, hafnium and titanium, having an ethylene/octene reactivity ratio up to 20, and a kinetic chain length up to 20 monomer units, in a continuously-fed backmixed reactor zone under conditions such that a mixture of at least two oligomer products is formed, the mixture including a hyperbranched oligomer having an average of at least 1.5 methine carbons per oligomer molecule, and having at least 40 methine carbons per one-thousand total carbons, and wherein at least 40 percent of the methine carbons are derived from the ethylene, and wherein the average number of carbons per molecule is from 25 to 100, and wherein at least 25 percent of the hyperbranched oligomer molecules have a vinyl group; and (b) a branched oligomer having an average number of carbons per molecule that is up to 20; (2) separating the hyperbranched oligomer and the branched oligomer; and (3) recovering the hyperbranched oligomer, the branched oligomer, or both.

In another aspect the invention provides a composition prepared by the defined process.

The following formulas are described as follows.

Formulas (I) and (II) represent generalized metallocene catalysts useful in the invention.

Formula (III) represents a generalized bis-phenylphoxy catalyst useful in the invention.

Formula (IV) represents a coordination-insertion catalyst of the formula $(L)ZrMe_2$ where (L)=2',2'''-(ethane-1,2-diyl-bis(oxy))bis(3-(3,6-di-tert-butyl-9H-carbazol-9-yl)-5'-fluoro-3'-methyl-5-(2,4,4-trimethyl-pentan-2-yl)-[1,1'-biphenyl]-2-ol).

Formula (V) represents a coordination-insertion catalyst of the formula $(L)ZrMe_2$ where (L)=3-(3,6-di-tert-butyl-9H-carbazol-9-yl)-2'-(2-((3'-(3,6-di-tert-butyl-9H-carbazol-9-yl)-5-fluoro-2'-hydroxy-5'-(2,4,4-trimethylpentan-2-yl)-[1,1'-biphenyl]-2-yl)oxy)ethoxy)-3',5'-difluoro-5-(2,4,4-trimethylpentan-2-yl)-[1,1'-biphenyl]-2-ol.

Formula (VI) represents a coordination-insertion catalyst of the formula $(L)ZrMe_2$ where (L)=3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol.

Formula (VII) represents a coordination-insertion catalyst of the formula $(L)HfMe_2$ where (L)=2',2'''-(ethane-1,2-diyl-bis(oxy))bis(3-(3,6-di-tert-butyl-9H-carbazol-9-yl)-3',5'-difluoro-5-(2,4,4-trimethylpentan-2-yl)-[1,1'-biphenyl]-2-ol).

Formula (VIII) represents a coordination-insertion catalyst of the formula $(L)ZrMe_2$ where (L)=2',2'''-(ethane-1,2-diylbis(oxy))bis(3-(3,6-di-tert-butyl-9H-carbazol-9-yl)-3',5'-difluoro-5-(2,4,4-trimethylpentan-2-yl)-[1,1'-biphenyl]-2-ol).

The inventive process offers advantages in that it may be employed to produce a hyperbranched product having particularly desirable rheological properties, including unexpectedly low viscosity for a given molecular weight, e.g., in some embodiments less than 60 centipoise (cP, 0.06 pascal second, Pa*s) at room temperature. It may also exhibit low pour point, in some embodiments less than −25° C. and high flash point, in some embodiments greater than 200° C. In particular, the process may be relatively inexpensive to carry out, both because it uses low-cost and readily-available starting materials, particularly ethylene, and is a continuous process that employs a conventional backmixed reactor. In particular, it employs a coordination-insertion catalyst selected from a group of catalyst families, and the catalyst may operate efficiently and over a wide thermal operating range, in some non-limiting embodiments withstanding temperatures exceeding 200° C.

The inventive process to prepare the hyperbranched products includes, generally, reaction of the starting monomer(s) to form a mixture of oligomers therefrom. As the term is used herein, "oligomers" are molecules, formed by consecutive addition of monomer or comonomer units, which have an average molecular size of no more than 50 units. The average size is calculated as the total number of incorporated comonomer units divided by the total number of oligomer molecules. Alternatively, another indication of molecular size is the average number of carbons per molecule, which is the total carbon count divided by the total number of molecules.

The starting monomer may be ethylene alone, or a proportion of an alpha-olefin comonomer may be included along with ethylene. If an alpha-olefin is to be included, it may be selected from, in non-limiting example, linear alpha-olefins having from 3 to 12 carbons, such as propylene, 1-butene, 1-pentene, 1-hexene, 1-heptene, 1-octene, 1-nonene, 1-decene, undecene, 1-dodecene, and combinations thereof. Smaller linear alpha-olefins having from 3 to 7 carbons are preferred, because they allow for a higher branch density of the final product oligomers. Branched alpha-olefins may also be employed in the process feed, and may include in non-limiting embodiments singly and multiply branched alpha-olefin monomers having from 5 to 16 carbons, wherein the first substituted carbon is at the "3" or greater position with respect to the vinyl, and combinations thereof. It is generally preferred that the first substitution be at the "4" or greater position.

It is noted that the ethylene/alpha-olefin reactivity ratio is distinct for any catalyst and is expected to vary with reaction temperature. For any given catalyst the ethylene-olefin reactivity ratio ($r_1$) is determined by performing a co-oligomerization at low conversion and observing the oligomer composition (F) resulting from a chosen monomer composition (f). Equation 1 hereinbelow is the relation between F, f, and $r_1$ which can be used to estimate $r_1$ from a single oligomerization or obtain a more statistically reliable value for $r_1$ from a series of oligomerizations:

$$(1-F_2)/F_2 = r_1(1-f_2)/f_2 \quad \text{(equation 1)}$$

FTIR or $^{13}C$ NMR measurements of oligomer composition (F) are typically used for reactivity ratio determination, with $^{13}C$ NMR being preferred. Alpha olefin monomer fractions ($f_2$) ranging from 33-66% are generally used for reactivity ratio determination, with a value of 50% being preferred. The preferred method for determining ethylene-olefin reactivity ratio involves an equimolar level of olefin and ethylene dissolved in a compatible solvent, such as an alkane, such that $f_1 = f_2 = \frac{1}{2}$. After a co-oligomerization of this mixture to a low conversion (<20%), the resulting oligomer compositions (F) are used in equation 1 to determine the reactivity ratio $r_1$.

Regardless of whether an alpha-olefin is employed, however, the catalyst selected for use in the invention has an ethylene/octene reactivity ratio that is up to 20, preferably from 1 to 20, more preferably from 1 to 12, and most preferably from 1 to 6. While ethylene/alpha-olefin reactivity ratios will, in general, normally vary according to processing temperature, the maximum ratios set herein applies for any and all processing temperatures.

Where an alpha-olefin other than octene will be included, it is additionally necessary to determine the reactivity ratio of ethylene to the specific selected alpha-olefin, in order to determine how much of the selected alpha-olefin monomer will be required to attain a targeted oligomer composition. A simple random copolymerization model relates the mole fraction of alpha-olefin monomer ($f_2$) to the mole fraction of alpha-olefin in the copolymer ($F_2$), where $r_1$ is the ratio of ethylene reactivity to alpha-olefin reactivity, based on equation 1 hereinabove, wherein $r_1$=ethylene reactivity/alpha-olefin reactivity; $F_2$=mole fraction alpha-olefin in the product oligomer; and $f_2$=mole fraction alpha-olefin monomer. Thus, for a given catalyst and with minimal experimentation, those skilled in the art will be able to easily determine the alpha-olefin monomer fraction ($f_2$) necessary to attain the desired alpha-olefin polymer content ($F_2$). For example, using the random incorporation model, if $r_1$=5, and 10 mol % alpha-olefin is desired in the target hyperbranched oligomer ($F_2$=0.10), then 36 mol % alpha-olefin ($f_2$=0.36) would be expected to be required in the free monomer in the vicinity of the catalyst. Conversely, an ethylene/alpha-olefin reactivity ratio of $r_1$=15 would result in 63% alpha-olefin monomer ($f_2$=0.63) required to ensure the same 10 mol % alpha-olefin content in the target hyperbranched oligomer. Because of in situ generation and consumption of alpha-olefins, the added alpha-olefin content may be determined by conventional mass balance calculations, taking into account both process feed and effluent streams.

Notwithstanding the above, it is preferred that only a minor amount of alpha-olefin is included, if any. That amount preferably ranges from 0 to 30 mol %; more preferably from 0 to 25 mol %; still more preferably from 0 to 20 mol %; yet more preferably from 0 to 10 mol %; and most preferably from 0 to 5 mol %. The amount of added alpha-olefin is most commonly preferred to be 0 mol % because added alpha-olefins tend to be more costly than the spectrum of alpha-olefins that are created in-situ. While ethylene feed streams often have a small fraction (less than 1 mol %) of alpha-olefin monomer impurities such as propylene, it is expected that such would have no significant detrimental effect on process operation or oligomer properties.

In the inventive process the selected starting monomer, or monomers, is/are contacted with a suitable coordination-insertion catalyst. As the term is used here, "coordination-insertion" means that the catalysts are capable of consecutively inserting unsaturated monomers, with the result that previously unsaturated carbons in the monomers and the oligomer become the backbone of a new oligomer. This catalyst may be selected, in one embodiment, from a wide variety of metal-ligand complexes. Those skilled in the art will be aware that catalyst performance varies with process temperature and also may vary with reaction mixture composition and conversion. Preferred catalysts are those exhibiting an activity level of 100,000 grams of oligomer per gram of catalyst metal (g/g cat). Also preferred are catalysts capable of producing a chain termination rate that results in product oligomer of a desired molecular weight and having a high fraction, preferably at least 25%, more preferably at least 50%, and most preferably at least 75%, of vinyl groups.

Kinetic chain length is also important in identifying particularly suitable catalysts for the present invention. Kinetic chain length is defined as the average number of monomeric repeat units incorporated by a catalyst before a chain transfer or chain growth terminating reaction. For linear coordination-insertion oligomers the kinetic chain length is equal to the number average degree of polymerization ($DP_n$), or the number average molecular weight ($M_n$) divided by the average repeat unit formula weight. For branched ethylene-based oligomers the kinetic chain length is more difficult to estimate because it depends on knowledge of the branching level. For an ethylene oligomerization the kinetic chain length may be determined from measurements of molecular weight and methines carbon (branching) level, as follows:

a) The number average degree of polymerization ($DP_n$) is calculated from number average molecular weight ($M_n$) divided by the repeat unit weight (28.1 g/mole), or from $^{13}C$ NMR measurement of Cn as described by equations 2-4 hereinbelow, where $DP_n=Cn/2$.
b) The average number of branches per oligomer molecule (Bn) is calculated from $^{13}C$ NMR data as described by equation 6 hereinbelow.
c) The kinetic chain length is derived from knowledge of $DP_n$ and Bn, and the fact that an ethylene oligomer molecule with b branch points is comprised of b+1 kinetic chains, wherein kinetic chain length=$DP_n/(1+Bn)$.

For a given catalyst, kinetic chain length may vary with monomer concentration and temperature, but in the present invention the kinetic chain length incorporated by the catalyst is desirably no more than 20 monomer units. Kinetic chain length is easiest to measure when linear oligomers are made intentionally and Bn is zero.

Examples of suitable coordination-insertion catalysts may generally include, in certain non-limiting embodiments, metal-ligand complexes including any of the metals zirconium, hafnium, or titanium, and preferably zirconium or hafnium. Among these catalysts may be certain metallocene catalysts, including certain constrained geometry catalysts, and bis-phenylphenoxy catalysts, provided that the selected catalyst meets the ethylene/octene reactivity ratio and kinetic chain length requirements as defined hereinabove.

The metallocene compounds useful herein are cyclopentadienyl derivatives of titanium, zirconium and hafnium. These metallocenes (e.g., titanocenes, zirconocenes and hafnocenes) may be represented by one of the following formulas:

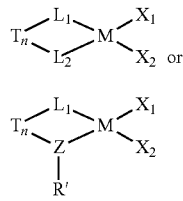

Formula I

Formula II wherein M is the metal center, and is a Group 4 metal, preferably titanium, zirconium or hafnium;

T is an optional bridging group which, if present, in preferred embodiments is selected from dialkylsilyl, diarylsilyl, dialkylmethyl, ethylenyl (—$CH_2$—$CH_2$—) or hydrocarbylethylenyl wherein one, two, three or four of the hydrogen atoms in ethylenyl are substituted by hydrocarbyl, where hydrocarbyl can be independently $C_1$ to $C_{16}$ alkyl or phenyl, tolyl, xylyl and the like, and when T is present, the catalyst represented can be in a racemic or a meso form;

$L_1$ and $L_2$ are the same or different cyclopentadienyl, indenyl, tetrahydroindenyl or fluorenyl rings, optionally substituted, that are each bonded to M, or $L_1$ and $L_2$ are the same or different cyclopentadienyl, indenyl, tetrahydroindenyl or fluorenyl, the rings of which are optionally substituted with one or more R groups, with any two adjacent R groups being joined to form a substituted or unsubstituted, saturated, partially unsaturated, or aromatic cyclic or polycyclic substituent;

Z is nitrogen, oxygen or phosphorus;

R' is a cyclic linear or branched $C_1$ to $C_{40}$ alkyl or substituted alkyl group; and $X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together form an olefin, diolefin or aryne ligand.

Among the metallocene compounds which can be used in this invention are stereorigid, chiral or asymmetric, bridged or non-bridged, or so-called "constrained geometry" metallocenes. See, for purpose of non-limiting example only and for further discussion of methods for preparation, U.S. Pat. Nos. 4,892,851; 5,017,714; 5,132,281; 5,155,080; 5,296,434; 5,278,264; 5,318,935; 5,969,070; 6,376,409; 6,380,120; 6,376,412; WO-A-(PCT/US92/10066); WO 99/07788; WO-A-93/19103; WO 01/48034; EP-A2-0 577 581; EP-A1-0 578 838; WO 99/29743, and also the academic literature, e.g., "The Influence of Aromatic Substituents on the Polymerization Behavior of Bridged Zirconocene Catalysts," Spaleck, W., et al., *Organometallics* 1994, Vol. 13, pp. 954-963; "ansa-Zirconocene Polymerization Catalysts with Annelated Ring Ligands—Effects on Catalytic Activity and Polymer Chain Lengths," Brintzinger, H., et al., *Organometallics* 1994, Vol. 13, pp. 964-970; "Constrained geometry complexes—Synthesis and applications," Braunschweig, H., et al., *Coordination Chemistry Reviews* 2006, 250, 2691-2720; and documents referred to therein, all of which are incorporated herein by reference in their entireties.

In certain particular embodiments, the selected catalyst may be a compound of Formula (III)

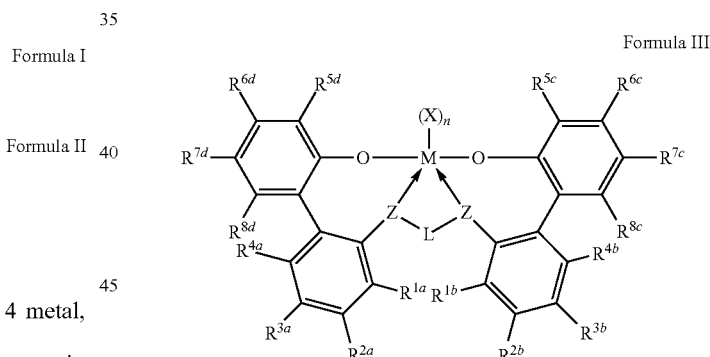

Formula III wherein M is titanium, zirconium, or hafnium, each independently being in a formal oxidation state of +2, +3, or +4; n is an integer of from 0 to 3, wherein when n is 0, X is absent; each X independently is a monodentate ligand that is neutral, monoanionic, or dianionic, or two X are taken together to form a bidentate ligand that is neutral, monoanionic, or dianionic; X and n are selected such that the metal-ligand complex of Formula (III) is, overall, neutral; each Z is independently O, S, N($C_1$-$C_{40}$)hydrocarbyl, or P($C_1$-$C_{40}$)hydrocarbyl; L is ($C_1$-$C_{40}$)hydrocarbylene or ($C_1$-$C_{40}$)heterohydrocarbylene, wherein the ($C_1$-$C_{40}$)hydrocarbylene has a portion that comprises a 2-carbon atom to 5-atom linker backbone linking the Z atoms in Formula (III) and the ($C_1$-$C_{40}$)heterohydrocarbylene has a portion that comprises a 2-atom to 5-atom linker backbone linking the Z atoms in Formula (III), wherein each atom of the 2-atom to 5-atom linker of the ($C_1$-$C_{40}$)heterohydrocarbylene independently is a carbon atom or a heteroatom, wherein each heteroatom independently is O, S, S(O), S(O)$_2$, Si(R$^C$)$_2$, Ge(R$^C$)$_2$, P(R$^P$), or N(R$^N$), wherein independently each R$^C$ is unsubstituted (C$_1$-C$_{18}$)hydrocarbyl or the two R$^C$ are taken together to form a (C$_2$-C$_{19}$)alkylene, each R$^P$ is unsubstituted (C$_1$-C$_{18}$)hydrocarbyl; and each R$^N$ is unsubstituted (C$_1$-C$_{18}$)hydrocarbyl, a hydrogen atom or absent; R$^{1a}$, R$^{2a}$, R$^{1b}$, and R$^{2b}$ independently is a hydrogen, (C$_1$-C$_{40}$)hydrocarbyl, (C$_1$-C$_{40}$)heterohydrocarbyl, N(R$^N$)$_2$, NO$_2$, OR$^C$, SR$^C$, Si(R$^C$)$_3$, Ge(R$^C$)$_3$, CN, CF$_3$, F$_3$CO, or halogen atom, and each of the others of R$^{1a}$, R$^{2a}$, R$^{1b}$, and R$^{2b}$ independently is a hydrogen, (C$_1$-C$_{40}$)hydrocarbyl, (C$_1$-C$_{40}$)heterohydrocarbyl, N(R$^N$)$_2$, NO$_2$, OR$^C$, SR$^C$, Si(R$^C$)$_3$, CN, CF$_3$, F$_3$CO or halogen atom; each of R$^{3a}$, R$^{4a}$, R$^{3b}$, R$^{4b}$, R$^{6c}$, R$^{7c}$, R$^{8c}$, R$^{6d}$, R$^{7d}$, and R$^{8d}$ independently is a hydrogen atom, (C$_1$-C$_{40}$)hydrocarbyl, (C$_1$-C$_{40}$)heterohydrocarbyl, Si(R$^C$)$_3$, Ge(R$^C$)$_3$, P(R$^P$)$_2$, N(R$^N$)$_2$, OR$^C$, SR$^C$, NO$_2$, CN, CF$_3$, RCS(O)—, RCS(O)$_2$—, (RC)$_2$C=N—, RCC(O)O—, RCOC(O)—, RCC(O)N(R)—, (RC)2NC(O)— or halogen atom; each of R$^{5c}$ and R$^{5d}$ is independently a (C$_6$-C$_{40}$)aryl or (C$_1$-C$_{40}$)heteroaryl; and each of the aforementioned aryl, heteroaryl, hydrocarbyl, heterohydrocarbyl, hydrocarbylene, and heterohydrocarbylene groups is independently unsubstituted or substituted with 1 to 5 more substituents R$^S$; and each R$^S$ is independently a halogen atom, polyfluoro substitution, perfluoro substitution, unsubstituted (C$_1$-C$_{18}$)alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the R$^S$ are taken together to form an unsubstituted (C$_1$-C$_{18}$)alkylene, wherein each R independently is an unsubstituted (C$_1$-C$_{18}$)alkyl.

In more particular embodiments, the catalyst may be selected from the compounds represented by Formulas (IV) to (VIII).

Formula IV

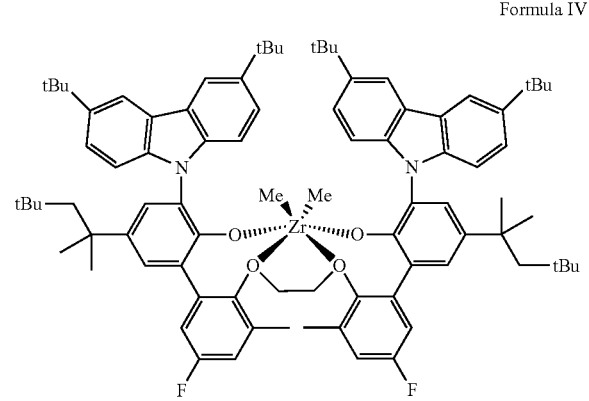

Formula V

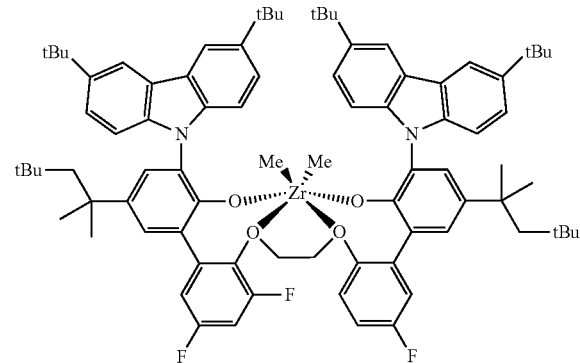

Formula VI

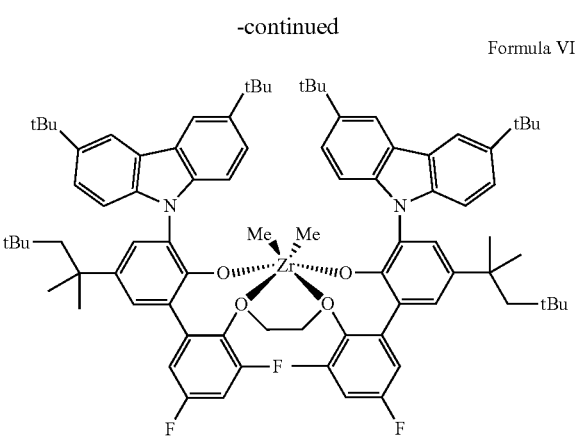

Formula VII

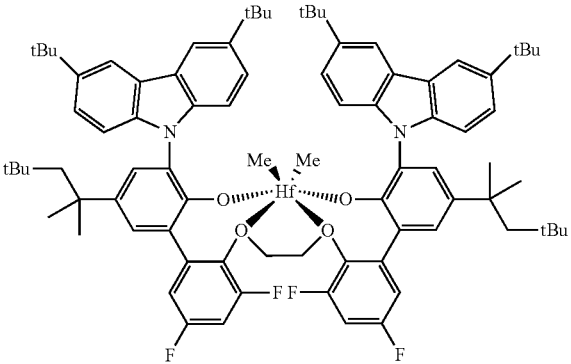

Formula VIII

Preparation of these bis-phenylphenoxy compounds may be by any means known to or envisioned by those skilled in the art, but in general involve means and methods such as are disclosed in, for example, U.S. Ser. No. PCT/US2012/0667700, filed Nov. 28, 2012, claiming priority to U.S. Provisional Application 61/581,418, filed Dec. 29, 2011 and U.S. Ser. No. 13/105,018, filed May 11, 2011, Publication Number 20110282018, claiming priority to U.S. Provisional Application 61/487,627, filed Mar. 25, 2011. Such is illustrated, in a non-limiting embodiment, in Example 10 herein, but those skilled in the art will recognize that similar and analogous processes may be used to prepare other useful bis-phenylphenoxy compounds falling within the given definition.

The reaction sequence occurring in the process of the invention may be defined according to the following reaction sequences:

1. The metal catalyst center (M) of the coordination-insertion catalyst mediates the co-oligomerization of ethylene with linear and/or branched alpha-olefins. It is noted that, even in the presence of added alpha-olefin comonomers, there will be a substantial amount of ethylene homopolymerization to make short linear alpha-olefin species. When the ethylene homopolymer forms in the presence of alpha-olefins, only the smaller oligomer products are anticipated to be linear, because the metal catalyst center M is preferably selected to have a high reactivity toward alpha-olefins. The co-oligomerization is preferably done in the absence of any chain transfer agent that would reduce the vinyl content of the oligomer. Undesired chain transfer agents include, for example, hydrogen ($H_2$) and metal alkyl groups such as AlR and ZnR, wherein Al is aluminum, Zn is zinc, and R is independently selected from the group consisting of linear alkyls, branched alkyls, and their alkoxy analogs.

The events included within this first step of the reaction sequence therefore may include:

1(a) homopolymerization of ethylene (reaction sequence 1)

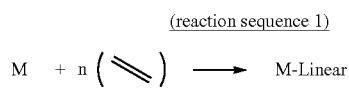

1(b) chain transfer or termination to linear alpha-olefins (reaction sequence 2)

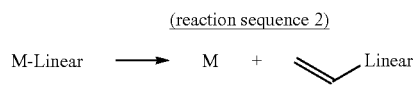

2. The co-oligomerization of ethylene and linear alpha-olefins results in branched products, some of which are branched alpha-olefin species that can further react to form hyperbranched oligomer. This random co-oligomerization of ethylene and alpha-olefins implies that the larger oligomer molecules will have more branch points than the smaller oligomer molecules, and that there will be a substantial presence of linear alpha-olefin species among the smaller oligomer products. Events included within this second step therefore include:

2(a) co-oligomerization of ethylene with linear alpha-olefins (reaction sequence 3)

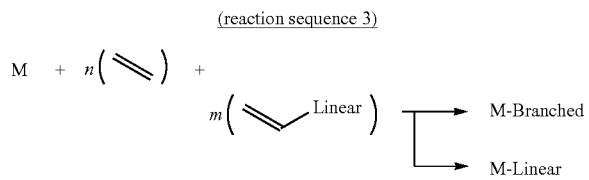

2(b) chain transfer or termination to form branched alpha-olefins (reaction sequence 4)

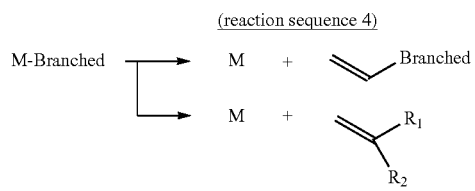

3. Finally, hyperbranching occurs when branched alpha-olefins are incorporated into an oligomer molecule, accordingly:

3(a)

(reaction sequence 5)

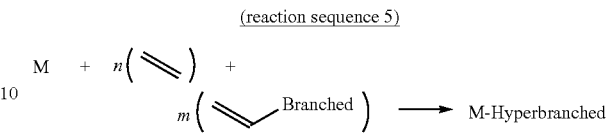

In carrying out the process of the invention it is desirable that the contact between the monomer(s) and the coordination-insertion catalyst occur in a continuously-fed back-mixed reactor zone. As the term is used herein, "backmixed reactor zone" refers to an environment wherein a reaction product is intermingled with unconverted reactor feeds. A continuous stirred tank reactor is preferred for this purpose, while it is noted that plug-flow reactors are specifically designed to prevent back-mixing. However, a loop reactor can accomplish a variable degree of backmixing by recycling a portion of reactor effluent to the feed of a plug-flow zone, with the recycle ratio moderating the degree of backmixing. Thus, plug-flow reactors are non-preferred, while a loop reactor with a plug flow zone is preferred. In the inventive process backmixing ensures reaction of already-produced oligomers with new feedstock, e.g., ethylene. It is this continuous contact that enables the oligomers to become branched via repeated olefin insertion.

Conditions under which the contact occurs in the continuously-fed, backmixed reactor zone may include a temperature desirably ranging from 0° C. to 250° C., more desirably from 25° C. to 200° C., and most desirably from 50° C. to 180° C.; an ethylene partial pressure desirably ranging from 15 psi (pounds per square inch, 103 kilopascals, kPa) to 500 psi (3450 kPa), more desirably from 30 psi (207 kPa) to 300 psi (2070 kPa), and most desirably from 50 psi (345 kPa) to 200 psi (1380 kPa); and a residence time desirably ranging from 1 minute (min) to 120 min, more desirably from 5 min to 60 min, and most desirably from 10 min to 30 min. A reactor system may be comprised of many low residence time reaction zones or a few high residence time reaction zones. Nonetheless, those skilled in the art will easily understand that alteration of parameters may be employed for reasons of convenience, alteration of yield, avoidance of undesirable side products or degradation, and the like.

The result of the process is production of at least two products, denominated a hyperbranched product and a branched product. For the sake of understanding, the term "hyperbranched oligomer" refers to the desired or target "hyperbranched" oil or grease, regardless of its order of production or relative proportion. Such materials are collectively termed herein as "utility fluids." By "hyperbranched" is meant that the oligomer molecules comprise a random distribution of linear chain segments joined together through methine carbons and having an average of at least 1.5 methine carbons per molecule. "Linear chain segments" are defined as the portion of a polymer or oligomer consisting of consecutive methylene carbons having a molecular formula of $[CH_2]_n$ where the average n is preferably from 3 to 13. Hyperbranching is present when the methine carbons are randomly located in the molecule and are not isolated to the main polymer backbone such as with a standard ethylene-olefin copolymer. $^{13}C$ NMR measurement of methine carbons may be used to determine the overall branching level. It is noted that, because of the nature of coordination-insertion, continued contact of feedstock and backmixed product with the catalyst would be expected to eventually result in true, completed polymerization, or an excessive level of branching, thereby forming a material that may contain a predominant amount of a non-hyperbranched product. Thus, the conditions of reaction, notably time, temperature and pressure, are desirably controlled so as to produce the desired hyperbranched oligomer. The final hyperbranched oligomer may be further characterized in that at least 40 percent of the methine carbons is derived from the ethylene; the average number of carbons per molecule is from 25 to 100; and at least 25 percent of the hyperbranched oligomer molecules has a vinyl group. In particular embodiments, the "hyperbranched" product has at least 55 methine carbons per one-thousand total carbons, and in more preferred embodiments, it has at least 70 methine carbons per one-thousand total carbons. This branching level is affected by both the incorporation of added alpha-olefins and the incorporation of in-situ generated olefins.

Additional desired characteristics of the hyperbranched products produced include embodiments wherein it is an oligomer oil having a pour point of less than 0° C., and embodiments wherein the oligomer oil has a pour point of less than −20° C. or even less than −25° C.

The "branched" product, which may be a single product or a group of products, may in many ways correspond to the "hyperbranched" product except that it, or they, will have an average number of carbons per molecule that is 20 or less. These "branched" product or products is/are referred to, therefore, as the "light olefin(s)." Because the process of the invention is designed to enable production particularly of the hyperbranched products, it is desirable to devolatilize the product mixture to separate the hyperbranched and branched products from one another, and thereby to recover the hyperbranched product.

A feature of the invention is that the hyperbranched product may also contain a desirable level of unsaturation, i.e., the at least 25 percent of vinyl endgroups, preferably at least 50 percent, and most preferably at least 90%, as discussed hereinabove. This effective functionalization enables subsequent processing as desired. For example, hydrogenation may be carried out in order to optimize the utility fluid composition for lubricant applications. Other types of subsequent processing, including but not limited to halogenations, etherification, hydroxylation, esterification, oxidation, hydroformylation, and combinations thereof, may also be carried out as desired.

It is important to note that the mechanism occurring in the present invention is coordination-insertion, where monomers add to a growing molecule through an organometallic center such that a molecular backbone is formed from carbons that originated from unsaturated carbons in the monomer units. Thus, an ethylene-only coordination-insertion oligomerization will produce branches with almost exclusively even numbers of carbons, and a coordination-insertion co-oligomerization involving ethylene and an olefin with an odd number of carbons (N) will result in branches with an odd number of carbons (N−2). This is distinct from "chain walking," which produces branches with a random distribution of both odd and even numbers of carbons. Thus, those skilled in the art will understand without further direction how to distinguish these via $^{13}$C NMR.

It is further suggested herein that the relatively high weight percent of product having methine branch carbons resulting from the coordination-insertion mechanism serves to ensure that a majority of the molecules are morphologically smaller and yet have the same molecular weight, which results in reduction in viscosity, while at the same time the absence of crystallinity with respect to molecular interaction offers excellent utility fluid behavior at colder temperatures. Finally, the relatively high level of unsaturation offers enhanced opportunity for later functionalization or product recycle. These advantages offer utility fluids, in the form of oils and greases, that are suitable for a wide variety of applications, such as for lubricants, hydraulic fluids, and dielectric fluids.

Determination of the characterizing properties listed hereinabove may be accomplished as follows:

For $^{13}$C NMR measurement, product samples are dissolved in 10 millimeter (mm) nuclear magnetic resonance (NMR) tubes in chloroform-d$_1$ (deuterated chloroform) to which 0.02 molar (M) chromium acetylacetonate, Cr(AcAc)$_3$, is added. The typical concentration is 0.50 grams per 2.4 milliliter (g/mL). The tubes are then heated in a heating block set at 50° C. The sample tubes are repeatedly vortexed and heated to achieve a homogeneous flowing fluid. For samples with visible wax present, tetrachloroethane-d$_2$ (deuterated tetrachloroethane) is used as the solvent instead of chloroform-d$_1$, and the sample preparation temperature is 90° C. $^{13}$C NMR spectra are taken on a Bruker Avance 400 megaherz (MHz) spectrophotometer equipped with a 10 mm cryoprobe. The following acquisition parameters are used: 5 seconds relaxation delay, 90 degree pulse of 13.1 milliseconds, 256 scans. The spectra are centered at 80 parts per million (ppm) with a spectral width of 250 ppm. All measurements are taken without sample spinning at either 50° C. (for chloroform-d$_1$ solutions) or 90° C. (for tetrachloroethane-d$_2$ solutions). The $^{13}$C NMR spectra are referenced to 77.3 ppm for chloroform-d$_1$ or 74.5 ppm for tetrachloroethane-d$_2$.

As is well-known to those skilled in the art, the $^{13}$C NMR spectra may be analyzed to determine the following quantities:

Number of methine carbons per one-thousand total carbons

Number of methyl carbons per one-thousand total carbons

Number of vinyl groups per one-thousand total carbons

Number of vinylidene groups per one-thousand total carbons

Number of vinylene groups per one-thousand total carbons

Based on the results obtained in the analysis of the $^{13}$C NMR spectra, the average number of carbons per molecule (Cn) may be determined using the following equation, which is based on the observation that every additional methine carbon, vinylidene group, and vinylene group results in an additional methyl carbon chain end:

$$1000/Cn = \text{methyl carbons} - \text{methine carbons} - \text{vinylidene groups} - \text{vinylene groups} \quad \text{(equation 2)}$$

Alternatively, the average number of carbons per molecule (Cn) may be determined for cases wherein each oligomer molecule has a single unsaturation which occurs upon chain termination. Exclusive terminal unsaturation is common when oligomerizations and polymerizations occur without the presence of added chain transfer agents, such as hydrogen or metal alkyls.

$$1000/Cn = \text{vinyl group} + \text{vinylidene group} + \text{vinylene group} \quad \text{(equation 3)}$$

An alternate determination of the average number of carbons per molecule (Cn) may be accomplished by simply averaging the two previous methods. The advantage of this method is that it no longer uses the vinylidene and vinylene group levels and gives the correct Cn even when no vinyls are present.

$$1000/Cn=(\text{methyl carbons}-\text{methine carbons}+\text{vinyl group})/2 \quad \text{(equation 4)}$$

Determination of the average level of branching, in terms of number of branches per one-thousand (1,000) carbon atoms (Bc), is equal to the methine carbon count per one-thousand total carbons.

$$Bc=\text{methine carbons} \quad \text{(equation 5)}$$

The number average degree of branching, in terms of number of branches per oligomer molecule (Bn), may be determined by multiplying Bc and Cn and resolving the one-thousand carbon basis.

$$Bn=Bc*Cn/1000 \quad \text{(equation 6)}$$

Determination of the mole fraction of oligomers having a vinyl group (Fv) is made as follows:

$$Fv=(\text{vinyl group})*Cn/1000 \quad \text{(equation 7)}$$

For the case where every molecule has a single unsaturation, Fv becomes:

$$Fv=(\text{vinyl group})/(\text{vinyl group}+\text{vinylidene group}+\text{vinylene group}) \quad \text{(equation 8)}$$

To determine the mole fraction of methine carbons that is derived from the ethylene feed rather than derived from added alpha-olefin monomer, mass balance calculations may be carried out. Those skilled in the art will be able to easily do this in the appropriate context with process variables taken into account. However, for some cases of added alpha-olefin monomer it is alternatively possible to measure or conservatively estimate this quantity. For example:

a. Added propylene monomer will result in methyl branches when incorporated into the oligomer backbone. A skilled practitioner can use $^{13}$C NMR spectral data to calculate the methyl branch level per one-thousand carbons. Each methyl branch is expected to be accompanied by a methine carbon that is not derived from ethylene. Therefore, calculation of the fraction of methine carbons derived from ethylene is given below:

b.

$$\text{Fraction of methines derived from ethylene}=(\text{methine carbons}-\text{methyl branches})/(\text{methine carbons}) \quad \text{(equation 9)}$$

c. Added hexene monomer will result in n-butyl branches when incorporated into the oligomer backbone. A skilled practitioner can use $^{13}$C NMR spectral data to calculate the n-butyl branch level per one-thousand carbons. However, some n-butyl branches are expected to occur in the absence of added hexene both as chain ends and ethylene-derived branches. Nonetheless, attribution of all n-butyl branches to added hexene incorporation results is a conservative estimate of methine carbons derived from ethylene as follows:

$$\text{Fraction of methines derived from ethylene}=(\text{methine carbons}-\text{n-butyl branches})/(\text{methine carbons}) \quad \text{(equation 10)}$$

The most definitive determination of methine fraction derived from ethylene is done using mass balance data around the oligomerization process. The mass balance data will indicate the net molar consumption of added monomer which can be a cumulative value for a semi-batch process or a rate value for a fully continuous process. The mass balance will also indicate the total moles of carbons as oligomers, which can be a cumulative value for a semi-batch process or a rate value for a fully continuous process.

$$\text{Net added monomer per one-thousand carbons}=1000*(\text{net added monomer moles})/(\text{total moles of carbons as oligomers}) \quad \text{(equation 11)}$$

The fraction of methines derived from ethylene is then calculated in the same manner as the methods that use only $^{13}$C NMR data:

$$\text{Fraction of methines derived from ethylene}=(\text{methine carbons}-\text{net added monomer per one-thousand carbons})/(\text{methine carbons}) \quad \text{(equation 12)}$$

Number average molecular weight (Mn) of the hyperbranched oligomer produced by the inventive process desirably ranges from 350 Daltons (Da) to 1,400 Da, more desirably from 350 Da to 1,000 Da, and most desirably from 350 Da to 700 Da. This may be determined using standard methods known to those skilled in the art, including gel permeation chromatography and gas chromatography. Furthermore, determination of Mn of oligomers using $^{13}$C NMR techniques is possible, taking into account the fact that Mn is about 14 times the average number of carbons per molecule (Cn). The exact method used to relate $^{13}$C NMR data to Mn is affected by monomer choice such as the feeding of branched and/or multiply unsaturated monomers. Nonetheless, those skilled in the art will easily comprehend how recipe changes may require amendment of this $^{13}$C NMR method to measure Mn.

Viscosity measurements may be carried out on, for example, a Brookfield CAP 2000+ viscometer with a 01 spindle. Approximately 70 microliters (µL) of the sample are added via a micropipette to the center of the plate which is held at 25° C. The spindle is dropped onto the sample and spun at 1000 revolutions per minute (rpm) for 40 seconds until the viscosity measurement stabilizes. The instrument is calibrated to a Cannon Instruments viscosity standard of 203 cP (0.203 Pa*s) at 25° C. For high viscosity samples, the spin rate is reduced to 300 rpm or until the percent torque drops to between 50% and 75%.

Flash point measurements may be carried out on, for example, an ERAFLASH instrument from ERA analytics with a high temperature attachment. An amount, 2 mL, of sample is added to the stainless steel sample cup via a micropipette and a stir bar is added. The sample cup and holder are placed into the sample chamber and the door is closed. Run parameters for the ERAFLASH include: stir rate=100 revolutions per minute (rpm), heat rate=10° C./min, with ignition every 2° C., temperature range=70° C., ignition time=2 milliseconds, air volume=10 mL between 150° C. and 300° C. After each sample the chamber is cleaned and the electrodes are cleaned with a wire brush typically provided by the manufacturer.

EXAMPLES 1-7 AND COMPARATIVE EXAMPLE A

Steady-State Continuous Stir Tank Reactor (CSTR) Oligomerizations

Small scale continuous flow solution oligomerizations are carried out in a computer controlled Autoclave Engineers™ reactor equipped with an internal stirrer and a single, stationary baffle operating at about a 9.5 minute (min) average residence time. Purified mixed alkanes solvent (Isopar™ E, available from ExxonMobil, Inc. consisting of C7-C9 isoalkanes) and ethylene are supplied at 1.00 gram per minute (g/min) to a 0.10 liter (L) reactor equipped with a jacket for temperature control, internal cooling coils, and thermocouple. For the various examples the reactor temperature set points range from 60° C. to 132° C. and are maintained by circulating heated oil through the jacket and cooling water through the internal cooling coils. A mass flow controller is used to deliver ethylene to the reactor.

The examples use various coordination-insertion catalysts which are activated with bis (octadecyl)methylammonium tetrakis(pentafluorophenyl) borate ([HNMe(C$_{18}$H$_{37}$)$_2$][B(C$_6$F$_5$)$_4$], abbreviated as BOMATBP). Modified methy aluminoxane (MMAO) is used as a scavenger, which moderates the effects of polar impurities on catalyst performance. The catalysts are delivered to the reactor as a 0.0001 mole/L solution in toluene; the catalyst activator, BOMATPB, is delivered to the reactor as a 0.00012 mole/L solution in Isopar™ E; and the MMAO scavenger is delivered as a 0.01 mole/L solution in Isopar™ E.

The Isopar™ solvent and solutions of catalyst, activator, and scavenger are fed into the reactor with syringe pumps, with a 1.2 molar ratio of BOMATPB and a 20:1 molar ratio of MMAO per catalyst metal such as Hf or Zr. The feed streams are introduced into the bottom of the reactor via two eductor tubes. The reactor is run liquid-full at 300 to 400 pounds per square inch gauge (psig, 2.1 to 2.7 megapascals, MPa) with vigorous stirring, while the products are removed through an exit line at the top of the reactor. The reactor effluent is electrically heat traced and insulated as it passes through an optical spectrophotometer cell that monitors the ethylene concentration (in grams per deciliter, g/dL). Oligomerization is stopped by the addition of a small amount of water and 2-propanol into the exit line along with a 2:1 mixture of Irgafos™ 168 and Irganox™ 1010 stabilizers, which are added at total level of 2000 parts per million (ppm) based on the mass of ethylene feed. This means that 0.2 g stabilizer is added for every 100 g of ethylene feed. The product is devolatilized to remove "light olefins," i.e., the "branched oligomer" having average carbon numbers of 20 or less, and a hyperbranched oligomer, which is an oligomeric oil, is then collected under an inert nitrogen atmosphere and dried in a temperature ramped vacuum oven for approximately 10 hours (h), with a final high temperature set point of 140° C.

Several catalysts are tested in the continuous flow reactor as shown in Tables 1 through 8. For each designated reaction temperature the catalyst feed rate is varied until a targeted steady-state ethylene conversion (i.e., oligomer production rate) is attained. A steady-state condition is defined as having been achieved when six (6) residence times have elapsed under constant feed with negligible change in ethylene conversion or pressure. The catalyst feed rate is reported in ppm, which is a ratio of catalyst metal weight per weight of total reactor contents. Quantities Cn and Bn are calculated from the $^{13}$C NMR spectra of the recovered oils, where Cn is the ratio of total carbons per unsaturation and Bn is the ratio of methine carbons per unsaturation. Because there are no added chain transfer agents such as hydrogen or metal alkyls, it is assumed that each oil molecule has a single unsaturation and therefore Cn is assumed to be the average number of carbons per molecule and Bn is assumed to be the average number of methine branch points per molecule. The quantity Pv is the percent of unsaturated groups that are vinyls and is also expected to be the vinyl endgroup percentage, because each oil molecule is assumed to have a single unsaturated endgroup.

Example 1

The coordination-insertion catalyst shown in Formula (I) is used at the temperatures shown in Table 1 and at an overall reactor feed rate of 7.43 g/min. Results are shown in Table 1, and "oligomer" in g/min in that table refers to production rate for the hyperbranched oligomer.

TABLE 1

| Temp (° C.) | Catalyst (ppm) | Oligomer (g/min) | Ethylene (g/dL) | Ethylene (% conv) | 13CNMR Data per 1000 carbons | | | Visc (Pa * s) | Flash Pt (° C.) | 13CNMR calculations | | |
|---|---|---|---|---|---|---|---|---|---|---|---|---|
| | | | | | methines | vinyl | vinylene | vinylidene | | | Cn | Bn | Pv |
| 132 | 0.26 | 0.61 | 0.20 | 97.7 | 41.28 | 20.58 | 3.18 | 1.94 | .160 | 199 | 38.9 | 1.61 | 80.1 |
| 80 | 0.28 | 0.68 | ~0 | >99 | 65.53 | 15.43 | 3.97 | 2.84 | .090 | 227 | 45.0 | 2.95 | 69.4 |
| 82 | 0.12 | 0.51 | 0.54 | 94.1 | 53.24 | 24.15 | 2.42 | 1.85 | .039 | 195 | 35.2 | 1.87 | 85.0 |
| 82 | 0.09 | 0.46 | 0.69 | 92.5 | 50.35 | 25.42 | 2.28 | 1.71 | .055 | 201 | 34.0 | 1.71 | 86.4 |

Example 2

The Formula (I) coordination-insertion catalyst is used at 70° C. with an overall reactor feed rate of 7.43 g/min and all other conditions employed in Example 1. The first two "steady-state" conditions (first two rows) have an ethylene concentration below the detection limit. Results are shown in Table 2.

TABLE 2

| Temp (° C.) | Catalyst (ppm) | Oligomer (g/min) | Ethylene (g/dL) | Ethylene (% conv) | 13CNMR Data per 1000 carbons | | | Visc (Pa * s) | Flash Pt (° C.) | 13CNMR calculations | | |
|---|---|---|---|---|---|---|---|---|---|---|---|---|
| | | | | | methines | vinyl | vinylene | vinylidene | | | Cn | Bn | Pv |
| 70 | 0.37 | 0.80 | ~0 | >99 | 79.2 | 8.54 | 5.99 | 3.90 | .167 | 218 | 54.3 | 4.30 | 46.3 |
| 70 | 0.74 | 0.85 | ~0 | >99 | 81.79 | 7.24 | 6.20 | 4.15 | .191 | 228 | 56.9 | 4.65 | 41.2 |
| 70 | 0.10 | 0.63 | 0.09 | 99.0 | 69.53 | 16.83 | 3.81 | 2.70 | .077 | 220 | 42.8 | 2.98 | 72.1 |
| 70 | 0.08 | 0.50 | 0.39 | 95.9 | 62.92 | 20.39 | 2.83 | 2.37 | .057 | 231 | 39.1 | 2.46 | 79.7 |

Example 3

The same catalyst as in previous examples is used at 60° C. with an overall reactor feed rate of 7.43 g/min. The last four steady-states have an ethylene concentration below the detection limit. Results are shown in Table 3.

TABLE 3

| Temp (° C.) | Catalyst (ppm) | Oligomer (g/min) | Ethylene (g/dL) | Ethylene (% conv) | 13CNMR Data per 1000 carbons | | | | Visc (Pa * s) | Flash Pt (° C.) | 13CNMR calculations | | |
|---|---|---|---|---|---|---|---|---|---|---|---|---|---|
| | | | | | methines | vinyl | vinylene | vinylidene | | | Cn | Bn | Pv |
| 60 | 0.09 | 0.53 | 0.42 | 95.6 | 67.71 | 22.03 | 3.06 | 2.37 | .047 | 211 | 36.4 | 2.47 | 80.2 |
| 60 | 0.11 | 0.68 | 0.06 | 99.4 | 75.95 | 16.15 | 4.05 | 2.96 | .074 | 215 | 43.2 | 3.28 | 69.7 |
| 60 | 0.07 | 0.38 | 1.03 | 89.1 | 60.74 | 25.82 | 2.35 | 1.95 | .035 | 213 | 33.2 | 2.02 | 85.7 |
| 60 | 1.10 | 0.88 | ~0 | >99 | 83.59 | 6.10 | 6.58 | 4.48 | .209 | 220 | 58.3 | 4.87 | 35.5 |
| 60 | 0.15 | 0.81 | ~0 | >99 | 80.4 | 11.99 | 5.16 | 3.66 | .119 | 206 | 48.1 | 3.86 | 57.6 |
| 60 | 0.12 | 0.78 | ~0 | >99 | 77.86 | 14.54 | 4.81 | 3.56 | .093 | 202 | 43.6 | 3.40 | 63.5 |
| 60 | 0.15 | 0.77 | ~0 | >99 | 80.06 | 11.95 | 4.83 | 3.38 | .119 | 228 | 49.6 | 3.97 | 59.3 |

Example 4

The Formula (II) coordination-insertion catalyst is used at 60° C. with an overall reactor feed rate of 7.43 g/min. The last three steady-states have an ethylene concentration below the detection limit. Results are shown in Table 4.

TABLE 4

| Temp (° C.) | Catalyst (ppm) | Oligomer (g/min) | Ethylene (g/dL) | Ethylene (% conv) | 13CNMR Data per 1000 carbons | | | | Visc (Pa * s) | Flash Pt (° C.) | 13CNMR calculations | | |
|---|---|---|---|---|---|---|---|---|---|---|---|---|---|
| | | | | | methines | vinyl | vinylene | vinylidene | | | Cn | Bn | Pv |
| 60 | 0.25 | 0.56 | 0.29 | 96.8 | 75.55 | 13.23 | 1.45 | 11.78 | .048 | 206.5 | 37.8 | 2.86 | 50.0 |
| 60 | 0.61 | 0.65 | ~0 | >99 | 79.33 | 9.75 | 1.68 | 13.28 | .056 | 202.5 | 40.5 | 3.21 | 39.5 |
| 60 | 1.23 | 0.67 | ~0 | >99 | 78.93 | 8.53 | 2.01 | 14.34 | .054 | 200.6 | 40.2 | 3.17 | 34.3 |
| 60 | 2.45 | 0.67 | ~0 | >99 | 79.18 | 7.04 | 1.78 | 16.28 | .049 | 206.6 | 39.8 | 3.15 | 28.0 |

Example 5

The Formula (III) coordination-insertion catalyst is used at 60° C. with an overall reactor feed rate of 7.35 g/min. Three of the steady-states have an ethylene concentration below the detection limit. Results are shown in Table 5.

TABLE 5

| Temp (° C.) | Catalyst (ppm) | Oligomer (g/min) | Ethylene (g/dL) | Ethylene (% conv) | 13CNMR Data per 1000 carbons | | | | Visc (Pa * s) | Flash Pt (° C.) | 13CNMR calculations | | |
|---|---|---|---|---|---|---|---|---|---|---|---|---|---|
| | | | | | methines | vinyl | vinylene | vinylidene | | | Cn | Bn | Pv |
| 60 | 0.25 | 0.39 | 0.21 | 97.9 | 87.25 | 20.60 | 3.74 | 5.97 | .033 | 210 | 33.0 | 2.88 | 68.0 |
| 60 | 0.62 | 0.48 | ~0 | >99 | 90.93 | 17.32 | 4.25 | 6.54 | .039 | 214 | 35.6 | 3.23 | 61.6 |
| 60 | 1.24 | 0.53 | ~0 | >99 | 94.78 | 15.49 | 4.47 | 6.85 | .047 | 216 | 37.3 | 3.54 | 57.8 |
| 60 | 2.48 | 0.58 | ~0 | >99 | 96.83 | 13.86 | 4.75 | 7.41 | .048 | 208 | 38.4 | 3.72 | 53.3 |
| 60 | 0.19 | 0.45 | 0.37 | 96.2 | 86.78 | 24.56 | 3.83 | 5.93 | .018 | — | 29.1 | 2.53 | 71.6 |
| 60 | 0.12 | 0.37 | 0.56 | 94.1 | 83.94 | 25.42 | 3.56 | 5.43 | .019 | — | 29.1 | 2.44 | 73.9 |
| 60 | 0.07 | 0.27 | 1.06 | 88.9 | 78.83 | 28.02 | 2.77 | 4.81 | .016 | — | 28.1 | 2.21 | 78.7 |

Example 6

The Formula (V) coordination-insertion catalyst is used at 60° C. with an overall reactor feed rate of 7.35 g/min. Results are shown in Table 6.

TABLE 6

| Temp (° C.) | Catalyst (ppm) | Oligomer (g/min) | Ethylene (g/dL) | Ethylene (% conv) | 13CNMR Data per 1000 carbons | | | | Visc (Pa * s) | Flash Pt (° C.) | 13CNMR calculations | | |
|---|---|---|---|---|---|---|---|---|---|---|---|---|---|
| | | | | | methines | vinyl | vinylene | vinylidene | | | Cn | Bn | Pv |
| 60 | 0.25 | 0.20 | 0.26 | 97.3 | 76.76 | 12.44 | 3.08 | 19.46 | .016 | — | 28.6 | 2.19 | 35.6 |
| 60 | 0.12 | 0.17 | 0.40 | 95.9 | 74.8 | 13.97 | 2.89 | 18.64 | .014 | — | 28.2 | 2.11 | 39.4 |

TABLE 6-continued

| Temp (° C.) | Catalyst (ppm) | Oligomer (g/min) | Ethylene (g/dL) | Ethylene (% conv) | 13CNMR Data per 1000 carbons ||| Visc (Pa * s) | Flash Pt (° C.) | 13CNMR calculations |||
|---|---|---|---|---|---|---|---|---|---|---|---|---|
| | | | | | methines | vinyl | vinylene | vinylidene | | | Cn | Bn | Pv |
| 60 | 0.07 | 0.11 | 0.59 | 94.0 | 71.57 | 15.57 | 2.61 | 17.91 | .015 | — | 27.7 | 1.98 | 43.1 |
| 60 | 0.62 | 0.22 | 0.14 | 98.5 | 74.39 | 10.87 | 3.33 | 20.01 | .017 | — | 29.2 | 2.17 | 31.8 |

Example 7 and Comparative Example A

The Formula (IV) coordination-insertion catalyst is used at 60° C. and 70° C. with an overall reactor feed rate of 7.35 g/min. The first steady-state has an ethylene concentration below the detection limit. Results are shown in Table 7. Notably, Comparative Example A shows less than 40 methines per 1000 carbons and insufficient methine branch carbons per molecule to qualify as a hyperbranched product. This low level of branching can be explained by the low ethylene conversion (90.3%) resulting in a higher free ethylene concentration (0.96 g/dl). This condition creates a less favorable environment for the re-incorporation of alpha-olefin product and results in less branching.

liquid feed addition, the reactor is heated up to the polymerization temperature set point. Ethylene is added to the reactor when at reaction temperature to maintain reaction pressure set point. Ethylene addition amounts are monitored by a micro-motion flow meter and integrated to give overall ethylene uptake after catalyst injection.

The catalyst and BOMATPB activator are mixed with the appropriate amount of purified toluene to achieve a desired molarity solution. The catalyst and activator are handled in an inert glove box, drawn into a syringe and pressure transferred into the catalyst shot tank. This is followed by three rinses of toluene, 5 mL each. Immediately after catalyst addition the run timer begins. Ethylene is then added continuously by the Camile™ to maintain reaction pressure

TABLE 7

| Ex or CEx | Temp (° C.) | Catalyst (ppm) | Oligomer (g/min)* | $C_2H_4$ (g/dL) | $C_2H_4$ (% conv) | $^{13}$C NMR Data per 1000 carbons |||| $^{13}$C NMR calculations |||
|---|---|---|---|---|---|---|---|---|---|---|---|---|
| | | | | | | Methines | Vinyl | Vinylene | Vinylidene | Cn | Bn | Pv |
| CEx A | 60 | 0.13 | 0.52 | 0.96 | 90.3 | 37.32 | 22.74 | 0.43 | 4.60 | 36.0 | 1.34 | 81.9 |
| Ex 7 | 70 | 1.21 | 0.82 | ~0 | >99 | 53.27 | 10.71 | 1.04 | 6.97 | 53.4 | 2.85 | 57.2 |

Examples 8-9 and Comparative Examples B-D

Semi-Batch Oligomerizations

Semi-batch oligomerizations are conducted in a 2 L Parr™ batch reactor. The reactor is heated by an electrical heating mantle, and is cooled by an internal serpentine cooling coil containing cooling water. Both the reactor and the heating/cooling system are controlled and monitored by a Camile™ TG process computer. The bottom of the reactor is fitted with a dump valve, which empties the reactor contents into a stainless steel dump pot, which is prefilled with a catalyst kill solution (typically 5 mL of an Irgafos™/Irganox™/toluene mixture).

The dump pot is vented to a 30 gallon blowdown tank, with both the pot and the tank $N_2$ purged. All chemicals used for oligomerization or catalyst makeup are run through purification columns to remove any impurities that may affect oligomerization. Liquid feeds such as alpha-olefin and solvents are passed through two columns, the first containing $Al_2O_3$ alumina, the second containing Q5, which is a copper reactant to scrub oxygen. Ethylene feed is passed through two columns, the first containing $Al_2O_3$ alumina and 4 Angstroms (Å) average pore size molecular sieves to remove water, the second containing Q5 reactant. The $N_2$, used for transfers, is passed through a single column containing $Al_2O_3$ alumina, 4 Å average pore size molecular sieves, and Q5 reactant.

The reactor is loaded first from the shot tank containing alpha-olefin, depending on desired reactor load. The shot tank is filled to the load set points by use of a lab scale to which the shot tank is mounted. Toluene or Isopar™ E solvent is added in the same manner as alpha-olefin. After set point in the reactor. If the ethylene uptake rate is low, then the headspace is purged, more catalyst and activator are added, and the ethylene pressure is re-established. After a designated time or ethylene uptake the agitator is stopped and the bottom dump valve opened to empty reactor contents to the dump pot. The dump pot contents are poured into trays placed in a lab hood where the solvent is evaporated off overnight. The trays containing the remaining polymer are then transferred to a vacuum oven, where they are heated up to 140° C. under vacuum to remove any remaining volatile species. After the trays cool to ambient temperature, the product is weighed for yield/efficiencies, and submitted for testing.

Examples 8-10 and Comparative Examples B AND C

A series of semi-batch oligomerizations are performed with a Formula (I) coordination-insertion catalyst at 80° C. and at several different pressures using 300 g toluene as a reaction solvent. The semibatch nature of the reaction is due to the continuous feeding of ethylene gas to maintain a constant pressure, and excess butene is purged out to allow the continued consumption of ethylene. No alpha-olefin comonomers are added to the reaction. The average number of carbons per product oligomers is calculated assuming all molecules have a single unsaturation group. Results are shown in Table 8. Comparative Examples B and C show insufficient branching to qualify as producing a hyperbranched product. This is because the reaction was stopped at a low yield. As the yield grows over time, there is an ever-increasing opportunity for branching and the branch creation is cumulative. The yield necessary for hyperbranching is dependent on the ethylene pressure, since branching is a result of the re-insertion of alpha-olefin product, which competes with ethylene insertion.

TABLE 8

| Ex or CEx | Pressure (KPa) | Catalyst (µmoles) | BOMATPB (µmoles) | Ethylene (g initial) | Ethylene (g added) | Yield (g) | 13C NMR Data per 1000 carbons | | | | | 13C NMR Calculations | | |
|---|---|---|---|---|---|---|---|---|---|---|---|---|---|---|
| | | | | | | | methines | vinyl | vinylene | vinylidene | n-butyl | Cn | Bn | Pv |
| Ex 8 | 31.9 | 1.8 | 2.16 | 35.4 | 500.7 | 256.4 | 54.03 | 28.60 | 2.23 | 3.00 | 17.20 | 29.6 | 1.60 | 84.5 |
| Ex 9 | 8.8 | 0.7 | 0.84 | 7.2 | 52 | 41.1 | 64.36 | 19.12 | 3.75 | 4.47 | 24.22 | 36.6 | 2.35 | 69.9 |
| Ex 10 | 8.8 | 2 | 2.4 | 8 | 126.5 | 108.6 | 72.94 | 13.23 | 4.67 | 5.10 | 28.63 | 43.5 | 3.17 | 57.5 |
| CEx B | 31.9 | 0.1 | 0.12 | 37 | 10.4 | 6.8 | 24.21 | 33.08 | 0.76 | 0.91 | 5.60 | 28.8 | 0.70 | 95.2 |
| CEx C | 16.8 | 0.1 | 0.12 | 18.9 | 32.1 | 11.2 | 40.43 | 32.48 | 0.81 | 1.46 | 9.62 | 28.8 | 1.16 | 93.5 |

Comparative Example D

A semi-batch oligomerization is performed with the Formula (I) catalyst at 80° C. with ethylene and 1-hexene as comonomers and no other added solvent except that used to deliver the catalyst. The semi-batch nature of the reaction is due to the continuous feeding of ethylene gas to maintain a constant pressure. However, the consumption is 1-hexene is low enough to have negligible impact on the ethylene to hexene ratio in the reaction mixture. The average number of carbons per product oligomers is calculated assuming all molecules have a single unsaturation group. The fraction of methines derived from ethylene is conservatively estimated from the $^{13}$C NMR data using the relation below, which indicates at least 14% of the methine carbons is derived from ethylene, where 14%=(108−93)/108. While the oligomer made in this comparative Example D has significant branching, those branches are largely due to incorporation of added 1-hexene rather than derived from ethylene.

The in situ alpha olefin creation by the catalyst is not significant when compared to the 1-hexene added to the reactor. Therefore only a small minority of the branched are expected to result from in situ olefin creation.

Fraction of methines derived from ethylene=(methine carbons−n-butyl branches)/(methine carbons)   (equation 10)

-continued

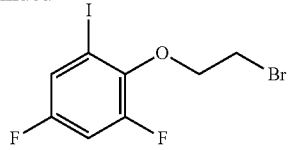

A mixture of 2-iodo-4,6-difluorophenol (10.00 g, 38.28 mmol) [prepared according to WO/2012/027448], 1,2-dibromoethane (144 g, 765 mmol), potassium carbonate (10.582 g, 76.566 mmol), and acetone (250 mL) is heated to reflux for 1 hour. The mixture is allowed to cool to room temperature and concentrated. The residue is partitioned in a 50/50 methylene chloride/water mixture and extracted with methylene chloride. The combined organic phases are washed with 2 N NaOH (300 mL), brine (300 mL), water (300 mL), dried over MgSO$_4$, filtered through a pad of silica gel and concentrated. The resulting oil is purified via column chromatography using a hexanes:ethyl acetate gradient to afford 12.5 g (86.8%) of the product as a slightly yellow oil.

TABLE 9

| Temp (° C.) | Pressure (KPa) | Hexene (g) | Catalyst (µmoles) | BOMATPB (µmoles) | Ethylene (g initial) | Ethylene (g added) | Yield (g) | 13C NMR Data per 1000 carbons | | | | | 13C NMR Calculations | | |
|---|---|---|---|---|---|---|---|---|---|---|---|---|---|---|---|
| | | | | | | | | methines | vinyl | vinylene | vinylidene | n-butyl | Cn | Bn | Pv |
| 80 | 7.3 | 236 | 6.1 | 7.34 | 5.5 | 21.6 | — | 108.11 | 9.74 | 14.73 | 2.67 | 93.01 | 36.9 | 3.98 | 35.9 |

Example 11

A coordination-insertion catalyst suitable for use in the present invention is prepared as following steps. Confirmation of each product is obtained via $^1$H NMR and $^{19}$F NMR.

(a) Step 1: Preparation of 2-(2-bromoethoxy)-1,5-difluoro-3-iodobenzene (reaction sequence 6)

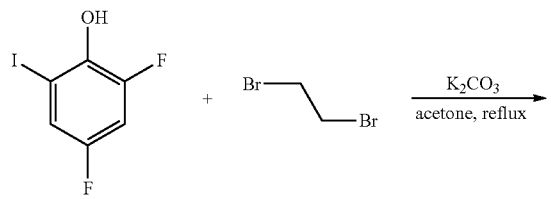

(b) Step 2: Preparation of 1,5-difluoro-2-(2-(4-fluoro-2-iodophenoxy)ethoxy)-3-iodobenzene (reaction sequence 7)

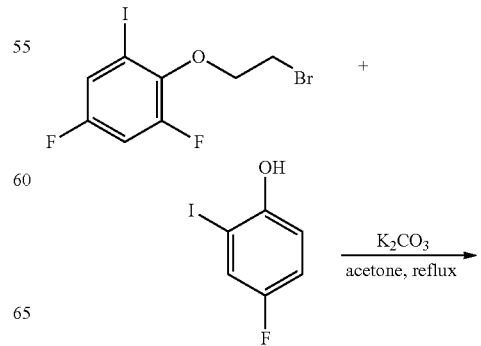

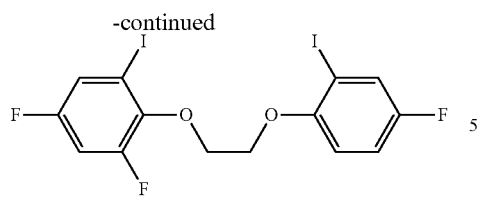

A mixture of 2-(2-bromoethoxy)-1,5-difluoro-3-iodobenzene (3.85 g, 10.6 mmol), 2-iodo-4-fluorophenol (2.525 g, 10.61 mmol) [prepared according to WO/2012/027448], potassium carbonate (3.094 g, 22.39 mmol), and acetone (80 mL) is heated to reflux and allowed to stir overnight. The mixture is cooled to room temperature and filtered. The cake is washed with acetone. The filtrate is concentrated to afford the crude as dark brown oil which as purified by column chromatography using 5% ethyl acetate in hexanes to afford 3.69 g (65.1%) of the product as a colorless oil.

(c) Step 3: Preparation of 3-(3,6-di-tert-butyl-9H-carbazol-9-yl)-2'-(2-((3'-(3,6-di-tert-butyl-9H-carbazol-9-yl)-5-fluoro-2'-hydroxy-5'-(2,4,4-trimethylpentan-2-yl)-[1,1'-biphenyl]-2-yl)oxy)ethoxy)-3',5'-difluoro-5-(2,4,4-trimethylpentan-2-yl)-[1,1'-biphenyl]-2-ol (reaction sequence 8)

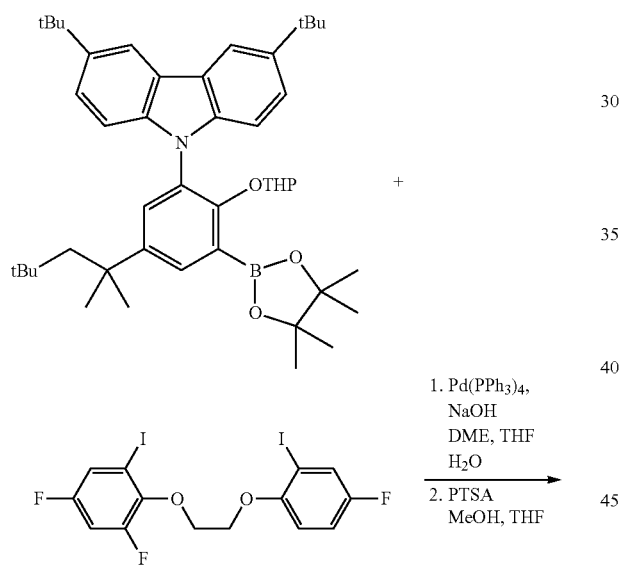

A mixture of 1,2-dimethoxyethane (69 mL), 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (4.00 g, 5.71 mmol) [prepared according to US2011/0282018], 1,5-difluoro-2-(2-(4-fluoro-2-iodophenoxy)ethoxy)-3-iodobenzene (1.41 g, 2.711 mmol), a solution of NaOH (0.6849 g, 17.12 mmol) in water (16 mL) and THF (40 mL) is purged with $N_2$ for 15 minutes, then $Pd(PPh_3)_4$ (0.1318 g, 0.1142 mmol) is added and heated to 85° C. overnight. The mixture is allowed to cool to room temperature and concentrated. The residue is taken up in methylene chloride (200 mL), washed with brine (200 mL), dried over anhydrous $MgSO_4$, filtered through a pad of silica gel, and concentrated to afford the crude protected ligand. To the crude is added tetrahydrofuran (50 mL), methanol (50 mL) and approximately 100 mg of p-toluenesulfonic acid monohydrate. The solution is heated to 60° C. overnight, then cooled and concentrated. To the crude ligand is added methylene chloride (200 mL), washed with brine (200 mL), dried over anhydrous $MgSO_4$, filtered through a pad of silica gel and concentrated to afford a brown crystalline powder. The solid is purified by column chromatography using a gradient of methylene chloride: hexanes to afford 1.77 g (52.4%) of the product as a white solid.

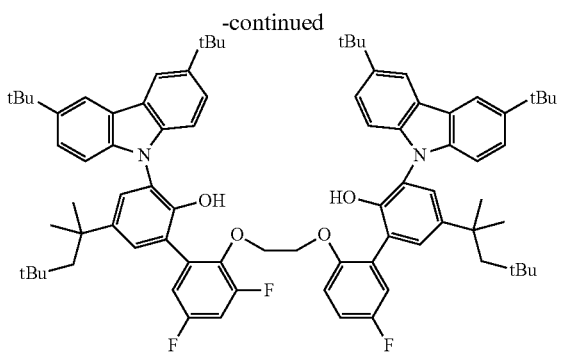

(d) Step 4: Formation of Metal-ligand Complex (reaction sequence 9)

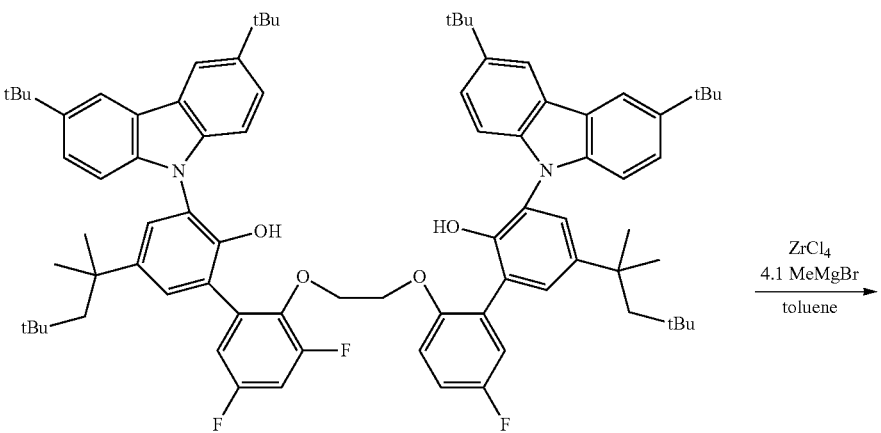

-continued

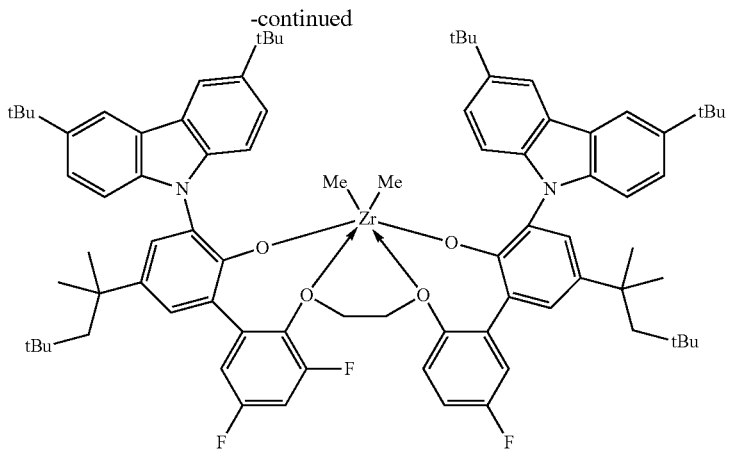

To a mixture of ZrCl$_4$ (0.086 g, 0.37 mmol) and ligand (0.456 g, 0.37 mmol) suspended in toluene (4 mL) was added 3M MeMgBr (0.52 mL, 1.56 mmol) in diethyl ether. After stirring for 1 hr at room temperature, hexane (10 mL) was added and the suspension was filtered giving colorless solution. Solvent was removed under reduced pressure to give 0.386 g (77.4%) of product metal-ligand complex.

The invention claimed is:

1. A process to prepare a utility fluid composition comprising:
   (1) contacting together ethylene and at least one coordination-insertion catalyst and, optionally, an alpha-olefin,
   wherein the coordination-insertion catalyst is a metal-ligand complex wherein the metal is selected from zirconium, hafnium and titanium,
   and has an ethylene/octene reactivity ratio up to 20, and a kinetic chain length up to 20 monomer units;
   in a continuously-fed backmixed reactor zone
   under conditions such that a mixture of at least two oligomer products is formed,
   the mixture including
   a hyperbranched oligomer having an average of at least 1.5 methine carbons per oligomer molecule,
      and having at least 40 methine carbons per one-thousand total carbons, and
      wherein at least 40 percent of the methine carbons is derived from the ethylene, and
      wherein the average number of carbons per molecule is from 25 to 100, and
      wherein at least 25 percent of the hyperbranched oligomer molecules has a vinyl group;
   and at least one branched oligomer having an average number of carbons per molecule that is less than 20;
   (2) separating the hyperbranched oligomer from the branched oligomer; and
   (3) recovering the hyperbranched oligomer, the branched oligomer, or both.

2. The process of claim 1 wherein the metal-ligand complex is a compound of the formula

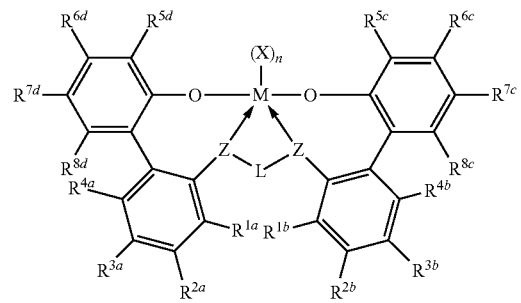

wherein M is titanium, zirconium, or hafnium, each independently being in a formal oxidation state of +2, +3, or +4;
n is an integer of from 0 to 3, wherein when n is 0, X is absent;
each X independently is a monodentate ligand that is neutral, monoanionic, or dianionic, or two X are taken together to form a bidentate ligand that is neutral, monoanionic, or dianionic;
X and n are selected such that the metal-ligand complex of the formula is, overall, neutral;
each Z is independently O, S, N(C$_1$-C$_{40}$)hydrocarbyl, or P(C$_1$-C$_{40}$)hydrocarbyl;
L is (C$_1$-C$_{40}$)hydrocarbylene or (C$_1$-C$_{40}$)heterohydrocarbylene, wherein the (C$_1$-C$_{40}$)-hydrocarbylene has a portion that comprises a 2-carbon atom linker backbone linking the Z atoms in the formula and the (C$_1$-C$_{40}$) heterohydrocarbylene has a portion that comprises a 2-atom atom linker backbone linking the Z atoms in the formula, wherein each atom of the 2-atom linker of the (C$_1$-C$_{40}$)-heterohydrocarbylene independently is a carbon atom or a heteroatom,
wherein each heteroatom independently is O, S, S(O), S(O)$_2$, Si(R$^C$)$_2$, Ge(R$^C$)$_2$, P(R$^P$), or N(R$^N$),
wherein independently each R$^C$ is unsubstituted (C$_1$-C$_{18}$) hydrocarbyl or the two R$^C$ are taken together to form a (C$_2$-C$_{19}$)alkylene,
each R$^P$ is unsubstituted (C$_1$-C$_{18}$)hydrocarbyl; and
each R$^N$ is unsubstituted (C$_1$-C$_{18}$)hydrocarbyl, a hydrogen atom or absent;
R$^{1a}$, R$^{2a}$, R$^{1b}$, and R$^{2b}$ independently is a hydrogen, (C$_1$-C$_{40}$)hydrocarbyl, (C$_1$-C$_{40}$)-heterohydrocarbyl, N(R$^N$)$_2$, NO$_2$, OR$^C$, SR$^C$, Si(R$^C$)$_3$, Ge(R$^C$)$_3$, CN, CF$_3$, F$_3$CO, or halogen atom, and each of the others of R$^{1a}$, $R^{2a}$, $R^{1b}$, and $R^{2b}$ independently is a hydrogen, $(C_1$-$C_{40})$hydrocarbyl, $(C_1$-$C_{40})$-heterohydrocarbyl, $N(R^N)_2$, $NO_2$, $OR^C$, $SR^C$, $Si(R^C)_3$, CN, $CF_3$, $F_3CO$ or halogen atom;

each of $R^{3a}$, $R^{4a}$, $R^{3b}$, $R^{4b}$, $R^{6c}$, $R^{7c}$, $R^{8c}$, $R^{6d}$, $R^{7d}$, and $R^{8d}$ independently is a hydrogen atom, $(C_1$-$C_{40})$hydrocarbyl, $(C_1$-$C_{40})$-heterohydrocarbyl, $Si(R^C)_3$, $Ge(R^C)_3$, $P(R^P)_2$, $N(R^N)_2$, $OR^C$, $SR^C$, $NO_2$, CN, $CF_3$, RCS(O)—, $RCS(O)_2$—, $(RC)_2C$=N—, RCC(O)O—, RCOC(O)—, RCC(O)N(R)—, $(RC)2NC(O)$— or halogen atom;

each of $R^{5c}$ and $R^{5d}$ is independently a $(C_6$-$C_{40})$aryl or $(C_1$-$C_{40})$heteroaryl;

each of the aforementioned aryl, heteroaryl, hydrocarbyl, heterohydrocarbyl, hydrocarbylene, and heterohydrocarbylene groups is independently unsubstituted or substituted with 1 to 5 more substituents $R^S$; and each $R^S$ is independently a halogen atom, polyfluoro substitution, perfluoro substitution, unsubstituted $(C_1$-$C_{18})$alkyl, $F_3C$—, $FCH_2O$—, $F_2HCO$—, $F_3CO$—, $R_3Si$—, $R_3Ge$—, RO—, RS—, RS(O)—, $RS(O)_2$—, $R_2P$—, $R_2N$—, $R_2C$=N—, NC—, RC(O)O—, ROC(O)—, RC(O)N(R)—, or $R_2NC(O)$—, or two of the $R^S$ are taken together to form an unsubstituted $(C_1$-$C_{18})$ alkylene, wherein each R independently is an unsubstituted $(C_1$-$C_{18})$alkyl.

3. The process of claim 1 wherein the coordination-insertion catalyst is selected from the group consisting of

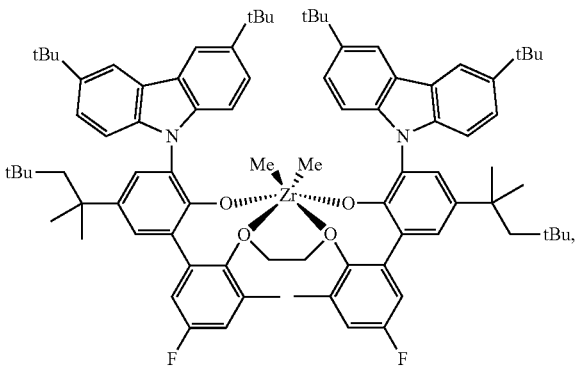

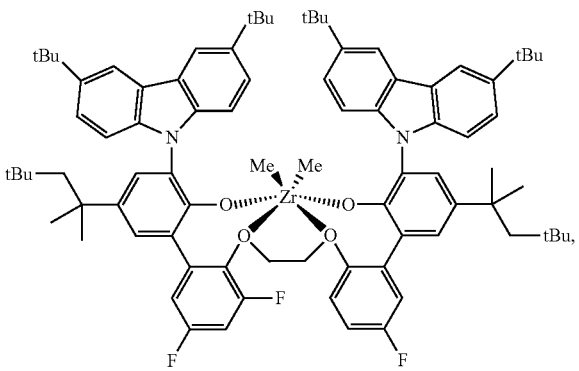

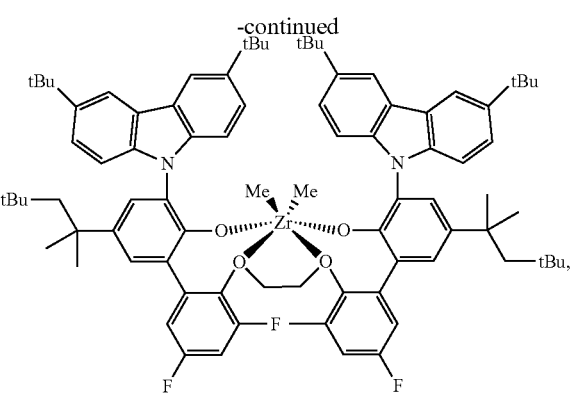

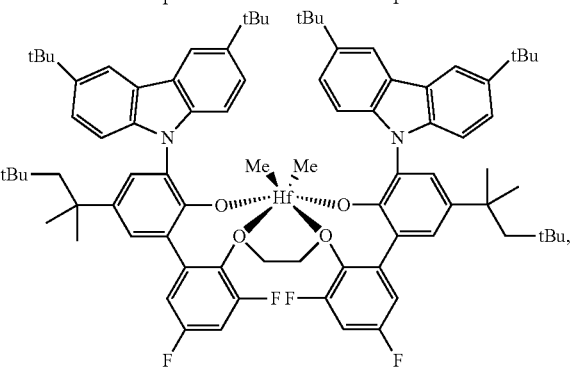

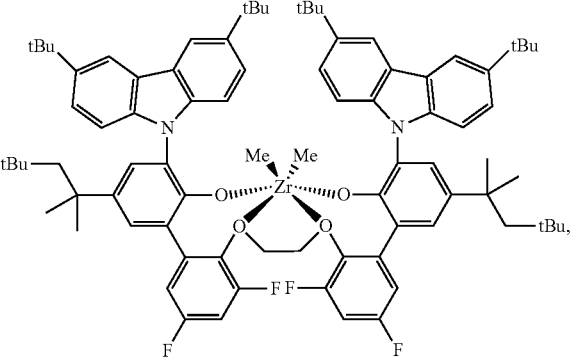

and combinations thereof.

4. The process of claim 1 wherein the metal-ligand complex is a compound of the formula

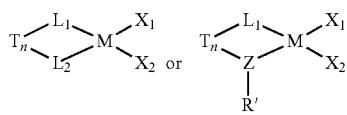

wherein M is the metal center, and is a Group 4 metal selected from titanium, zirconium or hafnium;

T is an optional bridging group which, if present, is selected from dialkylsilyl, diarylsilyl, dialkylmethyl, ethylenyl (—$CH_2$—$CH_2$—) or hydrocarbylethylenyl wherein one, two, three or four of the hydrogen atoms in ethylenyl are substituted by hydrocarbyl, where hydrocarbyl can be independently $C_1$ to $C_{16}$ alkyl or phenyl, tolyl, or xylyl, and when T is present, the catalyst represented can be in a racemic or a meso form;

$L_1$ and $L_2$ are the same or different cyclopentadienyl, indenyl, tetrahydroindenyl or fluorenyl rings, optionally substituted, that are each bonded to M, or $L_1$ and $L_2$ are the some or different cyclopentadienyl, indenyl, tetrahydroindenyl or fluorenyl, the rings of which are optionally substituted with one or more R groups, with any two adjacent R groups being optionally joined to form a substituted or unsubstituted, saturated, partially unsaturated, or aromatic cyclic or polycyclic substituent;

Z is nitrogen, oxygen or phosphorus;

R' is a cyclic linear or branched $C_1$ to $C_{40}$ alkyl or substituted alkyl group; and $X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from 3 to 20 carbon atoms; or both together form an olefin, diolefin or aryne ligand.

5. The process of claim 1, further comprising (4) performing a hydrogenation, halogenation, etherification, hydroxylation, esterification, oxidation, or hydroformylation of the hyperbranched oligomer, the branched oligomer, or both.

6. The process of claim 1, wherein at least 55 percent of the methine carbons is derived from the ethylene.

7. The process of claim 6, wherein at least 70 percent of the methine carbons is derived from the ethylene.

8. The process of claim 1 wherein at least 50 percent of the hyperbranched oligomer molecules has a vinyl group.

9. The process of claim 8 where at least 75 percent of the hyperbranched oligomer molecules has a vinyl group.

10. A utility fluid composition prepared by the process of claim 1.

* * * * *